United States Patent [19]

Eubanks et al.

[11] 4,111,982
[45] Sep. 5, 1978

[54] COPRODUCTION OF ACETIC AND PROPIONIC ACIDS

[75] Inventors: Lloyd S. Eubanks; Jerry L. Price, both of Texas City, Tex.

[73] Assignee: Monsanto Company, St. Louis, Mo.

[21] Appl. No.: 708,670

[22] Filed: Jul. 26, 1976

[51] Int. Cl.$^2$ .................... C07C 51/12; C07C 51/14
[52] U.S. Cl. .................................... 562/519; 562/522
[58] Field of Search .......................... 260/532, 533 AN

[56] References Cited

U.S. PATENT DOCUMENTS 3,579,552   5/1971   Craddock et al. .................... 260/413
3,769,329   10/1973  Paulik et al. ...................... 260/488 K

OTHER PUBLICATIONS

Research Disclosure, Dec. 1974, No. 128, p. 18.

Primary Examiner—Vivian Garner
Attorney, Agent, or Firm—James C. Bolding; Elizabeth F. Sporar

[57] ABSTRACT

An improved process for the simultaneous and continuous production of acetic and propionic acids in a single reactor wherein the rate of propionic acid production is enhanced over that which prevails when this acid is produced separately in the same reactor under the same conditions, said rate enhancement being achieved by the introduction of methanol at a critical rate.

7 Claims, No Drawings

COPRODUCTION OF ACETIC AND PROPIONIC ACIDS

BACKGROUND OF THE INVENTION

The present invention relates to the production of monocarboxylic acids. More particularly, it relates to the continuous production of acetic and propionic acids by simultaneous carbonylation of methanol and ethylene, respectively, in a single reactor.

A process for producing carboxylic acids and esters or mixtures of these compounds specifically by the reaction of an alcohol, or the ester, ether and halide derivative thereof, with carbon monoxide in the presence of a catalyst system consisting essentially of a rhodium compound and a halogen component is described in U.S. Pat. No. 3,769,329. The method is particularly suitable for the production of acetic acid from methanol and carbon monoxide in the liquid phase. Propionic acid is one of the many products which can be made from ethylene by using the liquid-phase process described and claimed in U.S. Pat. No. 3,579,552. This patent relates to producing a carboxylic acid by reacting an ethylenically unsaturated feedstock of from 2 to 30 carbon atoms with carbon monoxide and water in contact with a rhodium compound and a halogen promoter as the catalyst system.

The fact that acetic acid and propionic acid can be produced continuously in a single reactor by simultaneous carbonylation of ethylene and methanol using the catalyst system disclosed in the above-mentioned patents is known from "Research Disclosure," Dec. 1974, No. 128, Page 18. It would be expected from this disclosure that the two carbonylations would proceed independently in the same reactor environment with no interaction or influence of one upon the other. Accordingly, a substantially larger reactor would be required for the production of a predetermined quantity of both acids simultaneously than would be required for the production of either acid separately. However, it has now been discovered unexpectedly that the rate of reaction for the production of propionic acid is improved when this acid is produced from ethylene along with acetic acid being produced from methanol at specified conditions over the rate which prevails under the same conditions when it is produced separately. This makes possible the production of both acids simultaneously in a single reactor of the same size as would normally be employed to produce comparable quantities of either product separately.

SUMMARY OF THE INVENTION

According to the present invention, an improved process is provided for producing propionic acid and acetic acid simultaneously and continuously which comprises continuously contacting feed components comprising methanol, ethylene and water in a molar ratio from about 1:5:5 to about 100:1:1 together with carbon monoxide in a single reactor with a liquid reaction medium and a catalyst system consisting essentially of a rhodium compound and a halogen component which is bromine, iodine, a bromide or an iodide, said contacting being effected at temperatures from about 50° C to about 300° C and at partial pressures of carbon monoxide from 1 kg/cm² to 1056 kg/cm², controlling the rate of introduction of said methanol feed at or below $$5 \times 10^{10} e^{-7830/T} [R][I] \text{ gram-moles/liter-hr}$$

where
$T$ = reactor temperature, ° Kelvin,
$[R]$ = molarity of rhodium in the reactor and
$[I]$ = molarity of iodine in the reactor,
continuously withdrawing a portion of the liquid reaction mass from said reactor and separating therefrom acetic and propionic acids.

DESCRIPTION OF THE PREFERRED EMBODIMENTS

The process of the invention is a liquid-phase one wherein the feed components; ethylene, methanol, water and carbon monoxide are hydrocarbons, decane, dicosane, continuously contacted in a liquid reaction medium containing the catalyst system. The liquid reaction medium in which the reaction is conducted may be any solvent compatible with the catalyst system such as pure olefins, or saturated or unsaturated hydrocrbons, e.g., benzene, decae, eicosne, etc., or mixtures thereof with the desired carboxylic acids; pure alcohols, mixtures of the alcohol feedstock and/or the desired carboxylic acids; mixtures of pure olefins and pure alcohols; or mixtures of olefins, alcohols and the desired carboxylic acids. Water may optionally be added to the reaction medium in excess of the stoichiometric quantity required for the reaction as discussed below. The preferred solvent and liquid reaction medium is a monocarboxylic acid having 2 to 20 carbon atoms or a mixture of such acids such as acetic, propionic, nonanoic, naphthoic and elaidic acids. Particularly preferred is a mixture of the acids being produced, i.e., a mixture of acetic and propionic acids.

Generally, it is preferred that the process of the present invention be carried out in an acidic reaction medium. For the purpose of the present invention, an acidic reaction medium is defined as one in which an alkyl halide such as methyl iodide or ethyl iodide is present or will be formed. The alkyl halide may be added to the reaction medium as such or may be formed in situ within the reaction medium from the methanol feed and the halide present in the catalyst system.

The temperature at which the reaction is effected is in the range from about 50° to about 300° C with higher temperatures favoring higher reaction rates. A preferred temperature range is that from about 125° to about 225° C. Especially preferred temperatures are those from about 160° to about 200° C.

Reaction pressures may vary over a wide range. Partial pressures of carbon monoxide from 1 to 1056 kg/cm² and even higher can be employed. However, the process is particularly advantageous in that it can be carried out at lower partial pressures of carbon monoxide such as from 1.4 to 212 kg/cm² and even more preferably at carbon monoxide partial pressures from 3 to 71.3 kg/cm².

The rhodium-containing catalyst system employed in the process of the present invention is decribed in detail in U.S. Pat. Nos. 3,769,329 and 3,579,552, the disclosures of which are incorporated herein by reference. In general, such systems consist essentially of a rhodium compound and a halogen component. The active catalytic portion is the rhodium compound such as the salts, oxides, organometal compounds and coordination compounds of this metal. In the preferred catalyst system, the salts, oxides and carbonyls of rhodium consisting only of the metal and carbonyl moieties are employed. The halogen component of the catalyst system is supplied as the free halogen, e.g., bromine or iodine, or as a halogen compound such as hydrogen halide, alkyl or aryl halide, metal halide, ammonium, phosphonium, arsonium, stibonium halide, etc., wherein the halogen is either bromine or iodine. Iodine or iodide compounds are preferred for use as the halogen component of the catalyst system with hydrogen iodide or an alkyl iodide constituting the more preferred species. The halogen component may be charged to the reactor separately from the active metal compound or it may be incorporated into the active metal compound, e.g., $RhI_3$, $RhI[C_6H_5P]_3$, $Rh(CO)_2Br_2$, etc. Generally, however, it is preferred that the catalyst system contain as the halogen component an excess of halogen over that present as ligands in the rhodium complex. Ratios of halogen component to metal compound expressed as atoms of halogen to atoms of rhodium are in the range from 1:1 to 2500:1 but the preferred range is from 3 to 400 halogen atoms per rhodium atom.

The catalyst system may be preformed prior to charging to the reactor or it may be formed in situ in the reactor. The metal compound is preferably supplied as a catalyst solution which can also include liquid reactants, products and mixtures thereof which function as solvents or reaction media.

Concentrations of the rhodium compound of the catalyst system in the liquid phase between $10^{-6}$ and $10^{-1}$ mole/liter are normally employed, with the preferred range being $10^{-4}$ to $10^{-2}$ mole/liter. Higher concentrations even to the extent of 1 mole/liter may, however, be used if desired.

The concentration of the halogen component of the catalyst system may vary widely over the broad concentration range of $10^{-6}$ to 18 moles/liter, based on halogen atom. In the process of this invention, however, the preferred concentration range of halogen component is $10^{-4}$ to 2 moles/liter of catalyst solution.

A typical methanol carbonylation reaction selective to acetic acid requires stoichiometric quantities of the reactants, that is, at least one mole of carbon monoxide per methyl radical (molar basis). Similarly, a typical ethylene carbonylation reaction selective to propionic acid requires at least one mole of carbon monoxide and one mole of water per mole (equivalent) of ethylenically unsaturated linkage reacted. In either case, an excess of carbon monoxide over the aforesaid stoichiometric amount can be present and where water is a reactant in the ethylene carbonylation an excess of water can also be employed. In the coproduction of acetic and propionic acids, the molar ratio of the feed components will vary depending upon the ratio of the products desired. In general, however, the reactants are fed in sufficient quantities to provide molar ratios of methanol/ethylene reacted/water from about 1:5:5 to about 100:1:1 and preferably the ratio is maintained at from about 20:1:1 to about 1:1:1. Since the amount of water fed should be equivalent to the amount of ethylene reacted, the water concentration in the reaction system can be monitored and the water feed rate adjusted to maintain the water concentration at a constant level. Alternatively, the ethylene feed rate and the ethylene in the off gas can be measured to determine the amount of ethylene reacted and the molar water feed can be set equal to the moles of ethylene reacted.

A critical feature of the process is the rate at which methanol is introduced into the reactor. This reactant must be fed at a rate to insure that the rate at which the methanol reacts is below the maximum theoretical rate of reaction under the conditions of temperature, rhodium and iodine concentrations employed in the reactor. Based on a reaction rate model developed for the carbonylation of methanol using the above-described catalysts, it has been determined that methanol must be fed at a rate equal to or less than $$5 \times 10^{10} e^{-7830/T} [R][I] \text{ gram-moles/liter-hr}$$

where
 $T$ = reaction temperature, °Kelvin,
 $[R]$ = molarity of rhodium in the reactor, and
 $[I]$ = molarity of iodine in the reactor.
Rates in excess of this value do not provide the aforementioned advantages.

The carbonylation products of the reaction are continuously withdrawn8c either in the vapor state or by withdrawing a portion of the reaction mass, i.e., a solution from the reactor containing the catalyst system, unreacted feed, equilibrium components and the desired products. The desired products if in the vapor state can be condensed and subjected to further purification by conventional distillation techniques. Alternatively, when the desired products are withdrawn via the reaction mass, they can be separated therefrom by conventional distillation processing schemes to recover the crude carbonylation products so as to permit recycling of the catalyst-containing solution which contains the unreacted feed and also equilibrium 54 components. The crude products are then later purified by distillation. A preferred method of recovering the carbonylation products is described in U.S. Pat. No. 3,845,121. According to this method, a portion of the liquid reaction mass is withdrawn from the reactor or reaction zone and is passed without addition of het to a separation zone maintained at substantially lower pressure than the reaction zone. At least a portion of the carbonylation products will thus vaporize without any substantial decomposition of the liquid catalyst system. The vaporized products are then purified by distillation and the remaining liquid reaction mass is returned to the reactor or reaction zone.

The invention is illustrated in the following examples which, however, are not to be construed as limiting it in any manner whatsoever.

EXAMPLE 1

A one-liter, corrosion-resistant autoclave equipped with an agitator, a thermowell, a liquid sampling tap and a cooling coil and heated by means of an external heating mantle was employed as reactor. The reactor was flushed with carbon monoxide and charged with a solution of rhodium carbonyl iodide, hydrogen iodide (1.3 moles), water (10 moles) and acetic acid employed as a reaction medium. Rhodium concentration was 0.003 molar while iodine concentration was 1.3 molar. The autoclave was blocked in and a sufficient amount of CO was charged to provide a partial pressure of this reactant of about 8 kg/cm² at reaction conditions. The reactor was then heated to a temperature of about 185° C and 8.2 moles of methanol was charged.

After adjusting to a pressure of about 43 kg/cm², CO was fed to the reactor at a rate to maintain constant pressure. After about 9 minutes, ethylene was also fed to the reactor from a separate reservoir at an independently controlled average rate of 2.2 moles/1-hr based on the initial volume of the catalyst solution. The feed rate of ethylene was adjusted manually and was estimated from the pressure drop in the ethylene feed reservoir. Liquid samples were taken at periodic intervals during the run of approximately one hour duration and analyzed. Results of the analyses are presented in Table 1 below.

TABLE 1

| ELAPSED TIME* (Min.) | 27 | 43 | 62 |
|---|---|---|---|
| COMPONENT, WT. % | | | |
| Hydrogen Iodide | 0.67 | 0.54 | 1.99 |
| Water | 22.1 | 17.2 | 12.4 |
| Dimethyl Ether | 0.5 | 0.1 | 0 |
| Methanol | 1.5 | 0.7 | 0.3 |
| Methyl Iodide | 11.1 | 9.6 | 7.2 |
| Methyl Acetate | 14.7 | 6.4 | 0.5 |
| Acetic Acid | 49.6 | 59.6 | 65.7 |
| Propionic Acid | 0.6 | 6.0 | 13.0 |
| Ethyl Iodide | <0.1 | <0.1 | 1.0 |
| Ethyl Acetate | <0.1 | <0.1 | <0.1 |
| Methyl Propionate | <0.1 | 0.4 | <0.1 |

*From addition of methanol

Based on these analytical results, actual rates of methanol reacted which are essentially equivalent to the rates of methanol fed and ethylene reacted were calculated and found to be as follows:

| TIME (Min) | METHANOL REACTED (g-moles/liter-hr) | ETHYLENE REACTED (g-moles/liter-hr) |
|---|---|---|
| 27 | 7.9 | 0.33 |
| 43 | 6.1 | 3.3 |
| 62 | 5.0 | 4.3 |

Controlling the methanol feed as proposed in the present invention at a rate at or below the value of $$5 \times 10^{10} e^{-7830/T} [R][I] \text{ gram-moles/liter-hr}$$

where $T$ = temperature in °Kelvin, and $[R]$ and $[I]$ equal the molarity of rhodium and iodine, respectively, under the conditions employed in this example would constitute reacting (i.e., feeding) methanol at a rate equal to 7.3 gram-moles/liter-hr. It will be seen from the actual rates above that when the rate of methanol reacted (fed) is below this value, the rate of ethylene reacted (to propionic acid) is signficantly increased over that which prevails when the rate of methanol reacted (fed) exceeds this value.

EXAMPLE 2

The reactor employed for the carbonylation reactions in this example consisted of a corrosion-resistant vessel 15.3 cm. in I.D. and 25.4 cm. high provided with full length baffles, a six-blade turbine agitator and a 6.4 - cm. diameter sparge ring of 0.64 cm-titanium tubing with six equally spaced holes 0.08 cm. in diameter. Heat was provided by nichrome resistance wire wrappings on the reactor walls. An inlet valve for liquid reactants was provided in the bottom of the reactor while the gaseous reactants entered the reactor through the sparge ring. The effluent from the reaction was withdrawn either through a dip tube or a side tap near the top of the reactor.

The reactor was charged with a solution containing rhodium carbonyl iodide, methyl iodide, hydrogen iodide, water, acetic acid and propionic acid in proportions to provide molar concentrations of rhodium of 0.003, iodine of 1.1, and water of 10. The liquid level in the reactor was about 12.7 cm. and it was maintained at a temperature of 185° C while methanol was fed continuously into the solution at a rate of 13.5g moles/per hour and carbon monoxide was introduced continuously at a rate to maintain the pressure in the reactor at about 29 kg/cm². Portions of the liquid reaction mass were continuously removed from the reactor, subjected to an adiabatic flash, the non-vaporized liquid being returned to the reactor and the vaporized carbonylation products being condensed and separated by distillation to recover the acid product. Over a period of operation lasting 24 hours, during which the methanol feed rate was 5.9 gram-moles/liter-hr as compared to the 6.2 gram-moles/liter-hr given by the value $5 \times 10^{10} e^{-7830/T} [R][I]$ for the reaction conditions herein, the analyses of the products recovered showed that all the methanol feed was converted to acetic acid.

EXAMPLE 3

Following the same procedure and using the same reactor, the same temperature, the same catalyst solution and liquid reaction medium as those employed in Example 1, ethylene and water are charged continuously to the reactor at rates of 1g mole per hour and 0.96g mole per hour, respectively, while carbon monoxide is fed at a rate to maintain the same partial pressure of about 29 kg/cm². After feeding the reactants over a comparable period of time, recovery and analyses of the carbonylation product show that 96 percent of the ethylene feed is converted to propionic acid.

EXAMPLE 4

To the same reactor used in Examples 1 and 2, containing the same catalyst solution in the same concentration and in the same liquid reaction medium and operating under the same temperature and pressure as those examples, there was fed methanol at a rate of 13.5g moles per hour, ethylene at a rate of 1g mole per hour and water at a rate of 0.92g mole per hour and carbon monoxide. Recovery of the carbonylation product as described in the previous examples, separation thereof by distillation and analyses of the products showed that all of the methanol feed was converted to acetic acid and 92 percent of the ethylene feed was converted to propionic acid.

What is claimed is:

1. In a process whereby acetic and propionic acids are continuously and simultaneously produced by continuously contacting in a single reactor methanol, ethylene, water and carbon monoxide with a liquid reaction medium and a catalyst system consisting essentially of a rhodium compound and a halogen component which is iodine or an iodide compound at a temperature from about 50° to about 300° C and a partial pressure of carbon monoxide in the range from 1 to 1056 kg/cm², the improvement which comprises proportions molar proportins of methanol, ethylene and water from 1:5:5 to 100:1:1 and controlling the rate of introduction of methanol at or below $$5 \times 10^{10} e^{-7830/T} [R][I]$$

gram-moles/liter-hour, $T$ being reaction temperature in ° Kelvin and $[R]$ and $[I]$ being the molarity of rhodium and iodine, respectively, in the reactor.

2. The process of claim 1 wherein the molar ratio of methanol, ethylene and water is from about 20:1:1 to 1:1:1.

3. The process of claim 2 wherein said contacting is effected at a temperature from about 160° to about 220° C.

4. The process of claim 3 wherein the partial pressure of carbon monoxide is in the range from about 1.4 to about 212 kg/cm$^2$.

5. The process of claim 4 wherein said rhodium compound is rhodium carbonyl iodide and said iodine component is an alkyl iodide.

6. The process of claim 5 wherein said alkyl iodide is methyl iodide.

7. The process of claim 6 wherein said liquid reaction medium contains hydrogen iodide, acetic acid, propionic acid and water.

* * * * *